(12) United States Patent
Judd

(10) Patent No.: US 9,381,332 B2
(45) Date of Patent: Jul. 5, 2016

(54) NASAL DILATOR

(76) Inventor: Brian Judd, Campbell, CA (US)

( * ) Notice: Subject to any disclaimer, the term of this patent is extended or adjusted under 35 U.S.C. 154(b) by 417 days.

(21) Appl. No.: 12/916,538

(22) Filed: Oct. 30, 2010

(65) Prior Publication Data

US 2011/0270297 A1   Nov. 3, 2011

Related U.S. Application Data

(60) Provisional application No. 61/280,118, filed on Oct. 30, 2009.

(51) Int. Cl.
| | | |
|---|---|---|
| *A61M 29/00* | (2006.01) | |
| *A61F 5/08* | (2006.01) | |
| *A61F 5/56* | (2006.01) | |
| *B29C 45/00* | (2006.01) | |

(52) U.S. Cl.
CPC .................. *A61M 29/00* (2013.01); *A61F 5/08* (2013.01); *A61F 5/56* (2013.01); *B29C 45/00* (2013.01)

(58) Field of Classification Search
CPC ............ A61F 5/08; A61F 5/56; A61M 29/00; B29C 45/00
USPC ........ 606/199, 204.45; 128/848, 858, 207.18; 264/328.1
See application file for complete search history.

(56) References Cited

U.S. PATENT DOCUMENTS

| | | | | |
|---|---|---|---|---|
| 4,338,941 A | * | 7/1982 | Payton | .......................... 606/196 |
| RE35,408 E | * | 12/1996 | Petruson | ....................... 128/858 |
| 5,922,006 A | * | 7/1999 | Sugerman | ................ 606/204.45 |
| 6,635,214 B2 | * | 10/2003 | Rapacki et al. | ............... 264/250 |
| 7,055,523 B1 | * | 6/2006 | Brown | ...................... 128/206.11 |
| D550,347 S | * | 9/2007 | Norton | ......................... D24/106 |
| 2002/0153631 A1 | * | 10/2002 | Eckardt et al. | ............... 264/40.3 |
| 2006/0085027 A1 | * | 4/2006 | Santin et al. | .................. 606/199 |
| 2006/0266367 A1 | * | 11/2006 | Noce | ......................... 128/207.18 |
| 2007/0283936 A1 | * | 12/2007 | Athalye | ........................ 123/509 |
| 2007/0283963 A1 | * | 12/2007 | Sims | ........................ 128/206.18 |
| 2008/0119885 A1 | * | 5/2008 | Yazdi | .............................. 606/199 |
| 2009/0198268 A1 | * | 8/2009 | Case | ............................. 606/199 |
| 2010/0125295 A1 | * | 5/2010 | Wien | ............................ 606/196 |

* cited by examiner

*Primary Examiner* — Richard Louis
(74) *Attorney, Agent, or Firm* — Useful Arts IP

(57) ABSTRACT

A nasal dilator is provided that can be used primarily for exercise and secondarily rest and sleep. It may be designed as a resilient bridge between two arms that enter the nostril and then expand the nostril outward and upward. In one embodiment the dilator is flexible and the feet are brought together when inserted into the nose and when released they try to return outward and press against the nasal wall thus opening the nostrils. The feet may have an offset from the arm to deeper engage the nostril which helps to prevent the dilator from slipping off. Also the inside face of the feet and arm that run parallel to the septum wall may be generally flat to prevent irritation to the septum wall if pressed up against the septum wall. The easy to use and reusable nasal dilator can be used by athletes to better their performance through the improved utilization and flow of air through the nose.

10 Claims, 2 Drawing Sheets

Figure 9A:
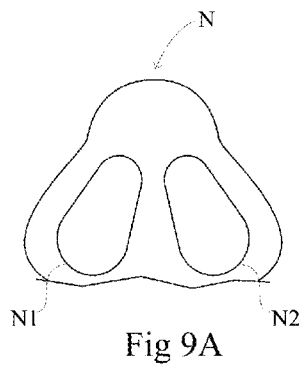

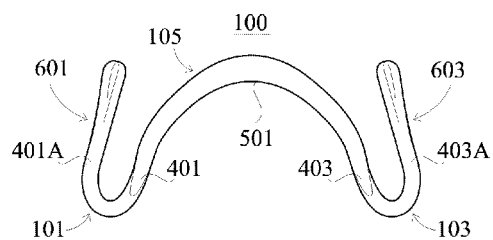
Fig 1
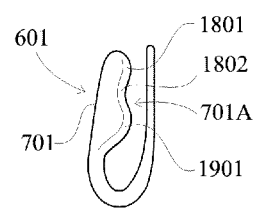
Fig 2
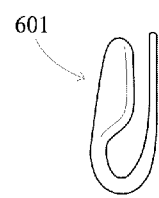
Fig 3
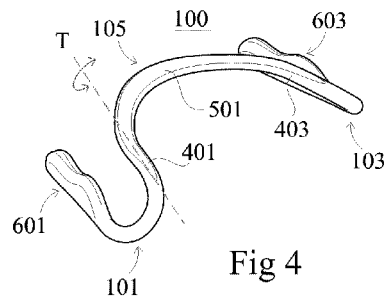
Fig 4
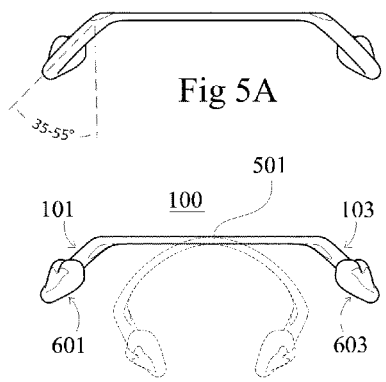
Fig 5A
Fig 5
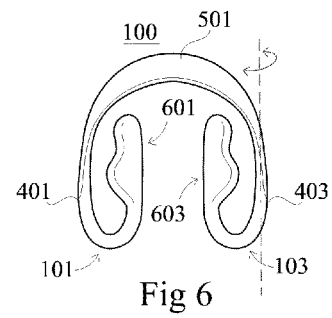
Fig 6
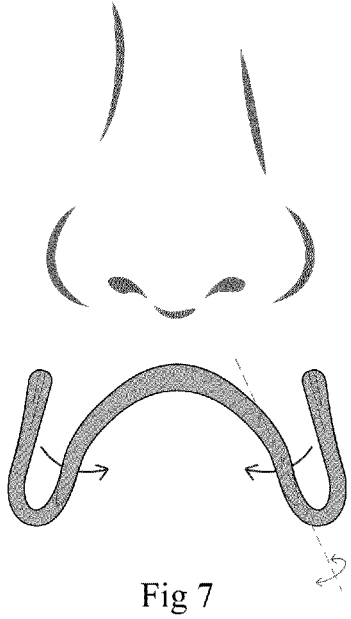
Fig 7
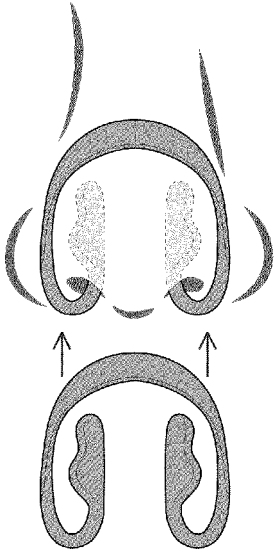
Fig 8

NASAL DILATOR

RELATED APPLICATION

This application claims benefit of U.S. Provisional Application Ser. No. 61/280,118 of the same inventor, entitled Nasal Dilator, filed Oct. 30, 2009, incorporated herein by reference.

BACKGROUND

1. Field of the Invention

This invention relates generally to breathing aids; more particularly, the present invention is in the technical field of nasal dilators

2. Background

There are a number of solutions that have been made to address the problems of obstructed breathing through ones nose. Focus has been primarily to address breathing obstruction during sleep which causes sleep apnea, a potentially dangerous medical condition.

A popular product on the market is sold under the brand Breathe Right™ nasal strips. A flexible strip of plastic that is attached to an oversized adhesive strip. The adhesive strip is placed traversing the bridge of the nose and bent to conform to the side of the nose. The plastic strip then tries to straighten but is resisted by the adhesive border which pulls up on the side of the nose therefore opening the nostrils. This is fine for sleeping when the breathing is light but cannot keep the nostril open comfortably under heavy load. Also the adhesive is not practical for exercise as sweat can weaken the adhesive and the wearer can have skin irritation from wearing the adhesive long-term.

U.S. Pat. No. 5,922,006 describes a clip that is malleable to position spacers in the top of the nostril that then prevents the nostril closure. The holder can then be bent and formed to fit the wearer. This creates a large obstruction in the nostril as the spacer must be large enough to expand the nostril to be effective. Further, there is a risk that the spacers can be dislodged and inhaled causing injury. Further, being malleable, the apparatus must be constantly adjusted to maintain placement and not fall off the nose, as there is no clamping mechanism. Further, this design does not easily accommodate the many sizes and shapes of noses. Spacers and holders would have to be in various sizes as one size will not fit around the many nose tip shapes.

U.S. patent application Ser. No. 11/630,895 describes a spring that does not put pressure on the top of the nose and holds two pivotal feet that spread the nose outward at the lower part of the nostril. Spreading the nose outward will not create sufficient force to hold open the nasal wall during exercise. The wall will tend to fold over it in the middle of the nostril. Creating two pivot points at the outer nostril walls makes the dilator easily rotate about those points requiring tape at the top of the nose to keep it securely in place as described. He further describes an generally L shaped arm with a U shape bent at 90 degrees at each end to enter the side of the nostril.

Some designs prefer wire products that are made to be springy but the wires can cause injury to the wearer as well as acute skin trauma from the sharp and focused pressure points imposed on the wearer of a wire dilator.

Other patents disclose flexible loops or balls that can be inserted in the nose. These create a constant pressure against the septum wall which is very sensitive and can cause irritation and discomfort.

There remains a need for a nasal dilator that can be comfortably worn, that can adapt to the variety of noses, that can be manufactured inexpensively and be reusable. A dilator that stays on the nose during exercise and can maintain nostril dilation during heavy breathing.

SUMMARY

The present invention advantageously fills the aforementioned deficiencies by providing a nasal dilator, made of resilient material for example, which advantageously allows the dilator to comfortably spread the nostrils up and out preventing collapse under heavy breathing.

In one embodiment, two U-shaped dilator arms are provided that insert into the nostrils and engage the nostril wall. These dilator arms are connected by a resilient bridge member that rests against the top of the nose. Further, nostril contacting portions may be provided on the dilator arms such that contact with the nostril occurs at a distance offset from the dilator arms. The contacting portions can be shaped to best engage the nostril wall. Further, the inside of the nostril arms may be provided with a generally flat shape and smooth surface so as not to irritate the septum wall if pressed inward against it.

The present invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DRAWING FIGURES

Figure 9B:
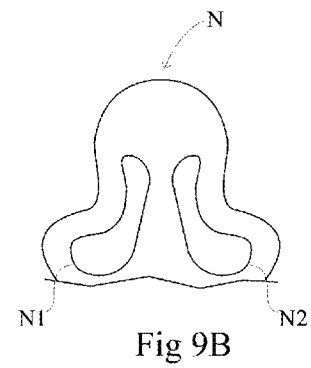
Figure 9C:
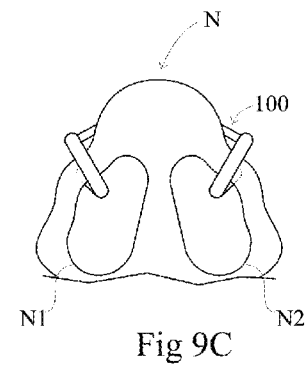
Figures 10, 11, 12:
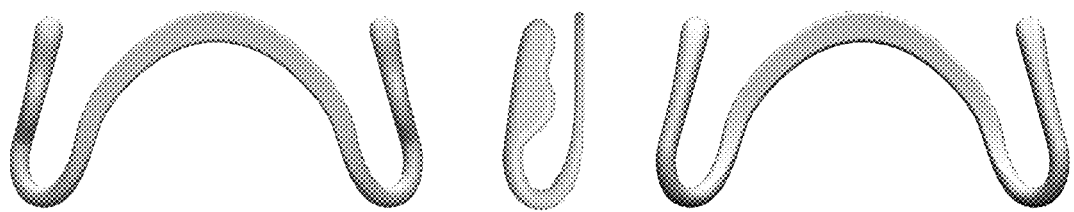
Figure 13:
Figure 14:
Figure 15:
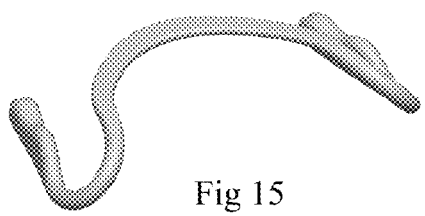

FIG. 1 is a front view of a nostril dilator in a relaxed state.
FIG. 2 is a perspective view of a nostril contacting portion.
FIG. 3 is a perspective view of another nostril contacting portion.
FIG. 4 is a perspective view of the nostril dilator of FIG. 1.
FIG. 5 is an end view of the nostril dilator of FIG. 1.
FIG. 5A is an end view of an opposite end of the nostril dilator of FIG. 5.
FIG. 6 is a front view of nostril dilator of FIG. 1 in a flexed state.
FIG. 7 is a diagram illustrating preparation of the nostril dilator for use.
FIG. 8 is a diagram illustrating further preparation for use and use of the nostril dilator.
FIG. 9A is a diagram illustrating a typical nostril condition during non-exertion.
FIG. 9B is a diagram illustrating a common nostril condition during strenuous exertion.
FIG. 9C is a diagram illustrating a nostril condition during use of the nostril dilator.
FIG. 10 is a shaded view corresponding to FIG. 1.
FIG. 11 is a shaded view corresponding to FIG. 2.
FIG. 12 is a shaded view from an opposite side of the nostril dilator of FIG. 1.
FIG. 13 is a shaded view corresponding to FIG. 5.
FIG. 14 is a shaded view corresponding to FIG. 5A.
FIG. 15 is a shaded view corresponding to FIG. 4.

DETAILED DESCRIPTION

Referring now to FIG. 1, a front view is shown of a nasal dilator, or nostril dilator, 100 in a relaxed state (as opposed to a flexed state that occurs during use, for example). First and second U-shaped dilator arms 101, 103 are joined by a bridge member 105, each U-shaped dilator arm having an inner arm 401, 403 (i.e., nearest a center point of the bridge member) and an outer arm 401A, 403A. In the relaxed state, the bridge member 105 joins the inner arms 401, 403 of the U-shaped dilator arms. Each U-shaped dilator arm may include a nostril contacting portion 601, 603. The bridge member 105 may have a flattened portion 501 for contacting a noise of the user, for example in a supratip region thereof. The flattened portion 501 increases both comfort and stability by distributing pressure throughout an increased area. The nostril dilator 100 as a whole may be generally W-shaped.

In some embodiments, the nostril dilator is a single-piece, molded nostril dilator formed, for example, by plastic injection molding. Examples of suitable plastics include Delrin™ brand plastic, acetal, and nylon. The nostril dilator may, however, be formed of any convenient material (metal, wood, resin, etc.) that has suitable spring characteristics as may be appreciated from the present description.

Referring to FIG. 2, a more detailed view is shown of a nostril contacting portion 601 of a U-shaped dilator arm. In accordance with one exemplary embodiment, the nostril contacting portion 601 has a forward surface 701A that is offset from an axis of the U-shaped dilator arm and a rearward surface 701 that is not offset. The rearward surface 701 is preferably smooth and flat to protect sensitive portions of the nostril in the event of an impact that may cause the rearward surface 701 to press against the septum. The offset forward surface 701A may undergo a transition or dip 1802, creating portions 1801 and 1901. The dip 1802 accommodates a common ridge that occurs inside the nostril wall. The portion 1901, which engages a lower inner portion of a human nostril, may be rounded. During use, the nostril conforms itself around the rounded portion 1901, promoting secure positioning of the nostril dilator.

Alternatively, as shown in FIG. 3, the forward surface 701A may also be relatively smooth, without the transition 1802 of FIG. 2.

A perspective view of the nostril dilator 100 is shown in FIG. 4. In the exemplary embodiment of FIG. 4, the flattened portion 501 of the bridge member 105 defines a reference plane. The U-shaped dilator arms 101, 103 occupy respective planes that are tilted with respect to the reference plane. In the illustrated embodiment, the respective planes have a tilt component relative to the reference plane of about 35 to 55 degrees, for example 45 degrees.

The bridge member 105 and the U-shaped dilator arms 101, 103 are configured to produce torsional springing actions about the inside arms 401, 403 of the U-shaped dilator arms 101, 103 adjoining the bridge member 105 when the outer arms 401A, 403A of the U-shaped dilator arms 101, 103 are squeezed toward one another. A torsional axis T for one of the U-shaped dilator arms is shown in FIG. 4.

An end view of the nostril dilator 100 is shown in FIG. 5. Shown in phantom lines is the nostril dilator 100 with the U-shaped dilator arms 101, 103 squeezed toward one another.

Referring to FIG. 6, a front view is shown of the nostril dilator 100 in a flexed position, with the U-shaped dilator arms 101, 103 squeezed toward one another, creating torsional flexion about the inside arms 401, 403 as indicated by the axis T. In the flexed position, the nostril dilator 100 is prepared to be placed in and on the user's nose, as shown in greater detail in FIG. 7 and FIG. 8. In FIG. 7, the nostril dilator is shown in a relaxed state in relation to the user's nose. Arrows indicate how the U-shaped dilator arms are to be squeezed toward one another. In FIG. 8, the nostril dilator is shown in a flexed state in relation to the user's nose. Arrows indicate how the flexed U-shaped dilator arms are to be inserted into the nostrils, with the bridge member being seated on the user's nose, for example in a supratip region thereof. During use, the supratip region of the user's nose may be slightly flattened in reaction to the torsional springing action of the U-shaped dilator arms, which may cause the nostrils to be slightly flared.

The effect of the nostril dilator during use may be appreciated with reference to FIG. 9A, FIG. 9B and FIG. 9C. FIG. 9A shows a nose N and nostrils n1 and n2 during normal breathing. FIG. 9B shows the nostrils having a tendency to collapse during heavy breathing. Surface drag as result of greater and more rapid air inflow causes the nostrils to partially or fully collapse. This collapse limits air inflow. FIG. 9C shows use of the nostril dilator 100 and its effect on the nostrils. Collapse of the nostrils as in FIG. 9B is prevented, with the result that air inflow is not limited. Increased air inflow capacity is especially evident during heavy exercise, such as running. Increased air availability increases utilization of the sinuses and diaphragm, resulting in increased performance and endurance. It is also believed to improve form and reduce the risk of injury.

The shape and configuration of the nostril dilator 100 may be further appreciated with reference to the shaded drawings of FIG. 10 through FIG. 15.

One method of making the nostril dilator is by injection molding. Fluid plastic material is injected into an injection mold having a channel defining a first U-shaped dilator arm, a second U-shaped dilator arm, and a bridge member joining the first dilator arm and the second dilator arm. The fluid plastic material is allowed to cool and solidify; and the mold is opened, releasing the nostril dilator.

Although the exemplary nostril dilator described and illustrated is for human use, nostril dilators for non-human use may follow the same or similar teachings. For example, the performance of racing animals such as horses, dogs, etc., may be enhanced using equine or canine nostril dilators following the same or similar principles as have been described.

While the present invention has been described above in terms of specific embodiments, it is to be understood that the invention is not limited to these disclosed embodiments. Many modifications and other embodiments of the invention will come to mind of those skilled in the art to which this invention pertains, and which are intended to be and are covered by both this disclosure and the appended claims.

It is indeed intended that the scope of the invention should be determined by proper interpretation and construction of the appended claims and their legal equivalents, as understood by those of skill in the art relying upon the disclosure in this specification and the attached drawings.

What is claimed is:

1. A nostril dilator comprising a bridge member for resting against the top of a nose, a first U-shaped dilator arm and a second U-shaped dilator arm for insertion into the nostrils and engagement of the nostrils wall, the first U-shaped dilator arm comprising an inner arm portion closest to a center point of the bridge member and an outer arm portion farthest away from the center point in a relaxed state of the nostril dilator, the second U-shaped dilator arm comprising an inner arm portion closest to a center point of the bridge member and an outer arm portion farthest away from the center point in a relaxed state of the nostril dilator, wherein the bridge member joins the inner arm portion of the first U-shaped dilator arm and the inner arm portion of the second U-shaped dilator arm, wherein the bridge member and the U-shaped dilator arms are configured so as to produce a torsional springing action about the inner arm portions when the outer arm portions of the U-shaped dilator arms are squeezed toward one another, creating torsional flexion about the respective inner arm portion for causing the nostrils to be slightly flared after the U-shaped dilator arms are inserted into the nostrils and released.

2. The apparatus of claim 1, wherein the nostril dilator is generally W-shaped.

3. The apparatus of claim 1, wherein the bridge member comprises a flattened portion for contacting a nose of a user in a supratip region thereof, the flattened portion defining a first plane.

4. The apparatus of claim 1, wherein the first and second U-shaped dilator arms occupy respective planes, the respective planes being tilted oppositely with respect to the first plane and having a tilt component in a rearward direction toward the user's nose of about 35 to 55 degrees.

5. The apparatus of claim 1, wherein the first and second U-shaped dilator arms comprise, respectively, first and second nostril contacting portions located at respective ends of the first and second U-shaped dilator arms away from the bridge member.

6. The apparatus of claim 5, wherein each of the nostril contacting portions comprises a smooth rearward surface and a contoured forward surface, the contoured forward surface being offset from an axis of the U-shaped dilator arm.

7. The apparatus of claim 6, wherein the contoured forward surface comprises a rounded portion for engaging a lower inner portion of a nostril.

8. The apparatus of claim 7, wherein the contoured forward surface undergoes a transition, creating an area of reduced dimensions compared to said rounded portion at an end portion of each of the first and second U-shaped dilator arms for accommodating a ridge inside the nostril wall.

9. The apparatus of claim 1, wherein the nostril dilator is a single-piece, molded nostril dilator.

10. A method of using a nostril dilator for providing increased air inflow capacity, the method comprising a user:
   providing a nostril dilator according to claim 1;
   inwardly pinching outer arm portions of the first dilator arm and the second dilator arm farthest away from a center point of the bridge member;
   inserting the first and second dilator arms into first and second nostrils of a nose of the user;
   seating the nostril dilator with the bridge member against a nose of the user; and
   releasing the nostril dilator, the first and second dilator arms causing flaring of the first and second nostrils.

* * * * *